United States Patent [19]

Jacobsen

[11] Patent Number: 5,329,352
[45] Date of Patent: Jul. 12, 1994

[54] SPECTROSCOPICALLY CORRELATED LIGHT SCANNING MICROSCOPY

[75] Inventor: Wolfgang Jacobsen, Cologne, Fed. Rep. of Germany

[73] Assignee: Bayer Aktiengesellschaft, Leverkusen, Fed. Rep. of Germany

[21] Appl. No.: 862,094

[22] Filed: Apr. 2, 1992

[30] Foreign Application Priority Data

Apr. 12, 1991 [DE] Fed. Rep. of Germany ....... 4111903

[51] Int. Cl.$^5$ .............................. G01J 3/02; G01J 3/44
[52] U.S. Cl. .................................... 356/301; 356/318; 356/328
[58] Field of Search ............... 356/300, 301, 326, 328, 356/317, 318; 364/526, 498

[56] References Cited

U.S. PATENT DOCUMENTS 5,192,980 3/1993 Dixon et al. ..................... 356/326

FOREIGN PATENT DOCUMENTS

WO91/05360 4/1991 PCT Int'l Appl. ............... 356/326

OTHER PUBLICATIONS

Applied Spectroscopy, vol. 44, No. 10, Dec. 1990, pp. 1679–1684.
Optical Engineering, vol. 28, No. 6, Jun. 1989, pp. 675–682.
Applied Optics, vol. 29, No. 33, Nov. 1990, pp. 4969–4980.
Measurement Science and Technology, vol. 1, No. 12, Dec. 1990, pp. 1311–1313.

Primary Examiner—F. L. Evans
Attorney, Agent, or Firm—Sprung Horn Kramer & Woods

[57] ABSTRACT

The present invention relates to a process for producing and correlating light microscope images and spectroscopic data resolved according to wavelength of a sample by scanning individual elements of the sample surface to be imaged once or twice with a confocal scanning light microscope, launching a portion of the light from the imaging beam path into a spectrometer and correlating the image data with the spectroscopic data by storing the spectroscopic data in a two-dimensional area, with one dimension being used to store the measured spectrum of the individual elements and the second dimension being activated by means of the light intensity diffusely reflected by the scanned elements or by means of a criterion obtained from the total data of the sample image by image processing. The advantage of said process is that the potential of a confocal scanning light microscope and of the various spectroscopic processes may be fully exploited.

11 Claims, 4 Drawing Sheets

SPECTROSCOPICALLY CORRELATED LIGHT SCANNING MICROSCOPY

BACKGROUND OF THE INVENTION

The present invention relates to a process for producing and correlating light microscope images and spectroscopic data resolved according to wavelength of a sample by means of confocal scanning light-microscopy and spectrometers.

It is known practice (Applied Physics 22 (1980), p.119) to produce light microscope images of transparent or semitransparent test objects using scanning light microscopy. If the beam path corresponds to the principle of the confocal light microscope (CLSM), optical sectional images are obtained, i.e. images of a narrow zone around the focal plane of the microscope lens. If the focal plane lies within the tested object, then owing to the confocal principle the intensities from the regions of the sample lying above and below are to a large extent eliminated. For some years now, appliances operating on said principle have been commercially available.

It is a further known practice to acquire data about the chemical structure of a test object by examining it using spectroscopic techniques, in particular by using light from the visible region of the spectrum or from regions close to the visible spectrum.

The combination of light-microscopy and spectroscopic techniques is also known from literature:

A concept already realized by most manufacturers of commercial confocal light microscopes is that of producing diffuse reflection images in the fluorescence contrast. For this purpose, the sample is illuminated by a monochromatic light source. There is inserted into the imaging beam path an optical filter which as completely as possible retains the light having the wavelength of the illuminating light source, so that only the fluorescent light having a longer wavelength reaches the photoelectric detector.

It is further known, from Microscopia Acta 79 (1977), 3, p.267-276, to add to the imaging beam path of a conventional light microscope a spectrograph which has been adjusted to a specific Raman line of a selected substance present in the test object. In said manner, a microscopic Raman dark field image of the object is produced. Said image reproduces the local distribution of the selected substance in the test object.

From Nature 347, (20.09.1990) p.301-303, it is known practice to use the concept of the confocal optical beam path in order to be able to record the complete Raman spectrum of a small pre-selectable measuring volume within the test object. For said purpose, the test object is illuminated by a laser by way of a stationary arrangement according to the concept of the confocal beam path, and the light passing through the aperture of the imaging beam path is analyzed in a Raman spectrometer. In said manner, the Raman spectrum of a selected measuring volume in the order of magnitude of 1 $\mu m^{**}3$ is obtained.

The drawback of all these processes known from literature which combine light-microscopy and spectroscopic techniques is that it is impossible to exploit the full potential of both techniques simultaneously:

The standard process of confocal fluorescence microscopy used up till now utilizes only the mean intensity of fluorescence transmitted by the measuring filter to build up the image. The fine details of the fluorescence spectrum are on the other hand not utilized. The process according to Microscopia Acta 79 (1977), 3, p.267-276, does not supply three-dimensional microscopic data, like confocal light microscopy, but only two-dimensional images and, moreover, of the data available in the Raman spectra it uses only those of a previously selected line when producing an image.

The process according to Nature 247, p.301-303, because of the absence of scanning microscope image production, likewise does not offer any three-dimensional microscopic data but does provide the entire Raman spectrum of the examined sample volume.

SUMMARY OF THE INVENTION

The aim therefore was to discover a process which allows the full potential of confocal scanning light microscopes and spectroscopic techniques to be exploited.

In particular, the aim was to discover a data-reducing type of correlation between the image of a sample obtained by the confocal scanning light microscope and its spectrum.

Said aim was achieved by carrying out the following steps:

a) scanning the individual elements of the sample surface to be imaged once or twice with a confocal scanning light microscope;

b) launching a portion of the light from the imaging beam path into a spectrometer;

c) correlating the image data with the spectroscopic data by storing the spectroscopic data in a two-dimensional area, with one dimension being used to store the measured spectrum of the individual elements and the second dimension being activated by means of the light intensity diffusely reflected by the scanned elements or by means of a criterion obtained from the total data of the sample image by image processing.

Further preferred forms of implementation are disclosed herein. For example, one- or two- dimensional arrangements of light sensitive semi-conductors or photoelectric multipliers are used as photoelectric detectors and a microscope with a monochromatic light source or a microscope with a light source emitting a continuous spectrum is used as a confocal scanning light microscope.

As a confocal scanning light microscope, all arrangements are suitable in which the sample piece is scanned by a focusing light beam and in which a portion of the transmitted or scattered light is imaged by an imaging optical beam path onto an aperture or onto a system of apertures and in which the portion of said light passing through the aperture is measured by a photoelectric detector and, with the aid of said measuring signal, an image of the entire sample piece is produced. In particular, arrangements based on the concept of the confocal laser scanning microscope (cf. e.g. T. Wilson Ed., Confocal Microscopy, Academic Press London etc. 1990) and arrangements based on the concept of the rotating aperture disk may be cited. The image of the sample piece produced in said manner may be both a sectional image perpendicular to the optical axis of the microscope as well as the image of a cutting plane of any desired orientation, in particular of a cutting plane which extends in the direction of the optical axis of the microscope.

The spectroscopic measuring processes may be any methods which are based on recording the wavelengthdependent intensity of visible light or of light having a wavelength in the vicinity of visible light, e.g. of 100 nm to 20 μm. Methods to be cited in particular are absorption spectroscopy in the ultraviolet, visible, near-infrared and infrared region as well as fluorescence and Raman spectroscopy. The excitation wavelength for fluorescence spectroscopy again lies in the region of 100 nm to 20 μm, preferably in the region of 300 nm to 700 nm. The excitation wavelength for Raman spectroscopy also lies in the region of 100 nm to 20 μm, preferably in the region of 250 nm to 1.5 μm.

As a simultaneously recording spectrometer, all arrangements may be cited which allow, for the entire wavelength range applicable to the spectroscopic process in question or for parts thereof, time resolution measurement of the radiant intensity contained in the measuring light per wavelength interval. A preferred arrangement is a single or multiple spectrograph, with a particularly preferred arrangement being a triple spectrograph arrangement with a line or monoplane photoelectric detector. A detector which is particularly preferred is a two-dimensional CCD array (charge coupled device).

It is astonishing that, despite the confocal light microscope having been in commercial use for many years, no full combination with spectroscopic techniques has as yet been achieved. However, an immediate and direct combination, without special data reducing measures, leads to enormous data rates and data volumes, as the following numerical example demonstrates: spectroscopic intensity measurements with 8 bit resolution and at 1,024 wavelength interpolation points lead, in conjunction with the production of an image of 512*512 pixels, to a data volume of 268 MB per image and hence, given an image frequency of 1 Hz, to a data rate of 268 MB/sec.

The process according to the invention allows the simultaneous or consecutive production of a confocal, light-microscope, optical sectional image on the one hand and a set of spectroscopic intensity distributions on the other hand, and does so in such a way that, on the basis of said data, the associated mean spectrum of the spectroscopic process used may then be indicated for each suitably selected portion of this optical sectional image.

In other words, separate data may be acquired relating to the chemical structure of the morphological structural elements which become evident as a result of the differing contrast in the light microscope image. Examples are material identification of the individual phases in multiphase polymers, location and identification of additives and impurities in polymers or location of active substances in biological preparations.

The process according to the invention is explained in greater detail using the following examples and the drawings.

DETAILED DESCRIPTION OF THE INVENTION

Figure 1:
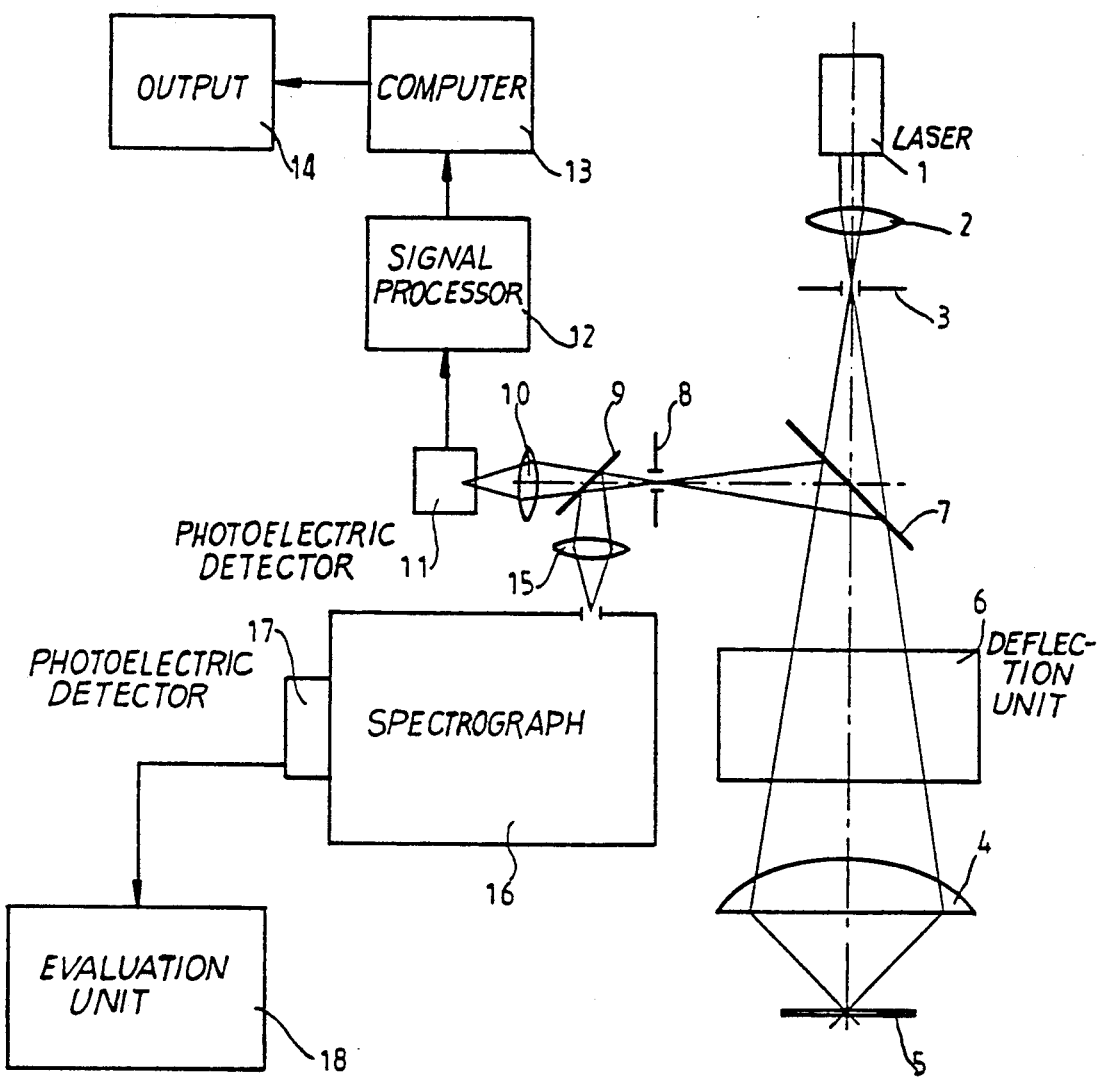
FIG. 1 shows the basic set-up for effecting the process.

The basic manner of effecting the process is described using the example of a confocal laser scanning microscope:

The light emitted by the laser 1 is focused by a focusing lens 2 onto the entrance aperture 3. Said aperture is imaged by the microscope lens 4 onto or into the sample 5 to be examined. The deflection unit 6 lying between aperture and lens leads to linear scanning of the selected sample piece by said laser beam.

The light diffusely reflected by the sample is collected again by the microscope lens 4 and focused by the beam splitter 7 onto a second aperture 8. A portion of the light passing through said aperture is guided through the beam splitter 9 by way of a further lens 10 to a photoelectric detector 11. The electric signal produced by the photoelectric detector is amplified and converted from analog to digital in the signal processing unit 12. The digitized CLSM image may be further processed and stored in a computer system 13 and may be displayed at an output device 14.

The portion of the backscatter intensity deflected by the beam splitter 9 is imaged by the lens 15 onto the entrance slit of the spectrograph 16. From said portion, the spectrograph 16 simultaneously produces a spectrum analysis which is detected by the line or monoplane photoelectric detector 17. The electric signal of said photoelectric detector is amplified in the spectroscopic evaluation unit 18.

In both examples, the combination of a confocal laser scanning microscope with a Raman spectrograph is described. The examples differ from one another in their manner of recording the spectroscopic measuring data.

Example 1 describes deflection of the Raman scattered light by means of a rotating mirror.

Figure 2:
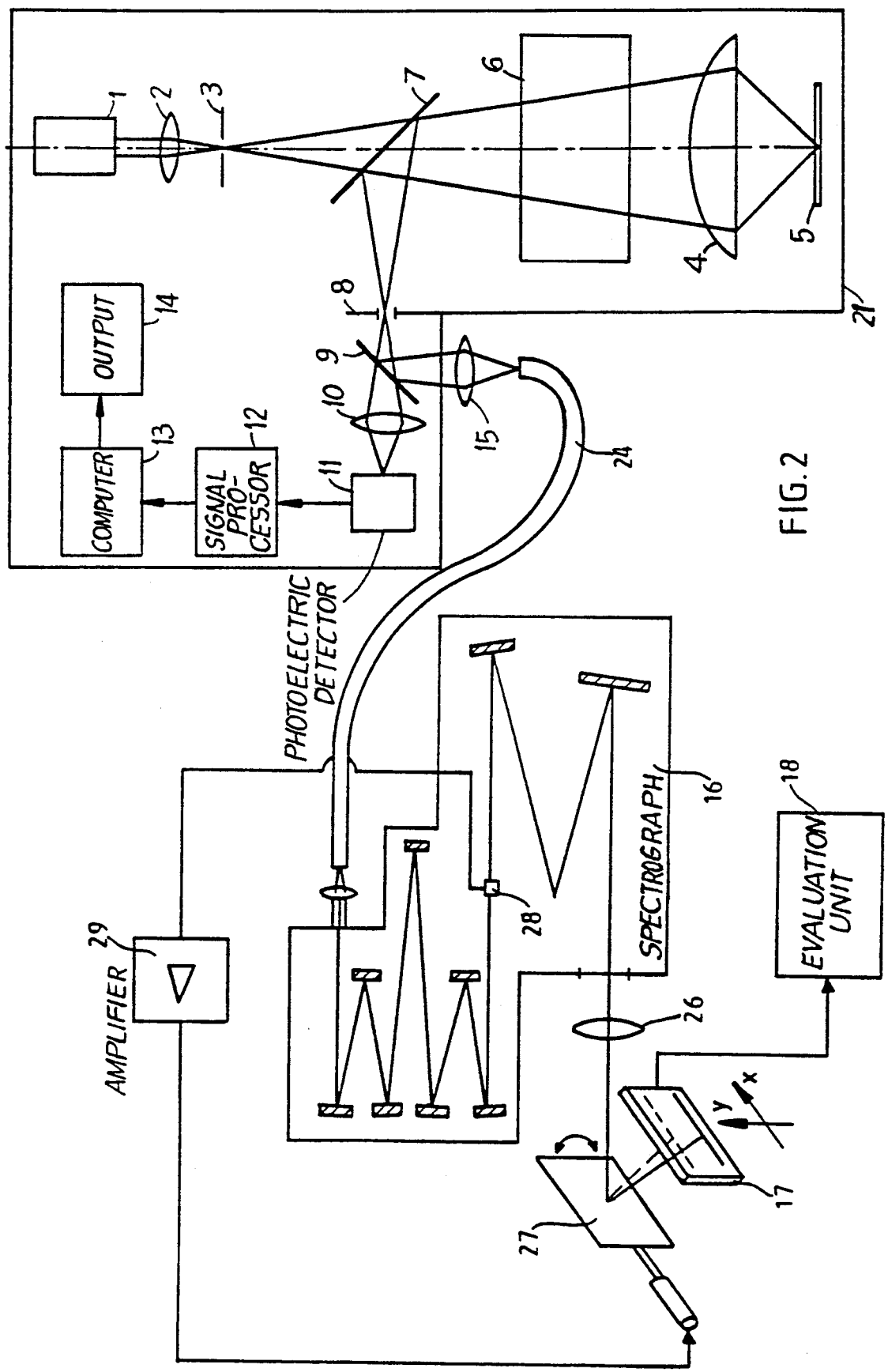
FIG. 2 illustrates how the process is effected with mechanical allocation of the spectra to the pixels.

The technical implementation details for this example are illustrated in FIG. 2.

A commercial CLSM 21 is combined with a commercial triple spectrograph 16 in that a portion of the measuring light passing through the measuring aperture is separated from the measuring channel of the CLSM by a beam splitter 9 and introduced by way of the optical fibres 24 into the spectrograph. The first two stages of the spectrograph retain the elastically (i.e. with no wavelength change) scattered laser light. What remains is the light scattered by fluorescence or the Raman effect. Said light is subjected to spectrum analysis in the third stage of the spectrograph and imaged onto the cooled two-dimensional CCD array 17. The local coordinates on the CCD array, along which spectrum analysis of the measuring light is effected, are referred to hereinafter as xy.

Situated between the exit slit of the spectrograph and the CCD array is a relay lens 26 with an electromotively controlled rotating mirror 27. The rotating mirror allows the measuring light to be deflected in the y direction of the array, perpendicular to the x direction mentioned above.

Said rotating mirror is then controlled by means of the intensity of the light scattered elastically in the sample, said intensity being measured in the second stage of the spectrograph 16 by the photoelectric detector 28. On the other hand, this is also the variable which produces the contrast in the conventional CLSM diffuse reflection image. The signal of the photoelectric detector is amplified in the amplifier 29.

The Raman (and fluorescence) intensity measured during a complete scanning process for producing a CLSM image in the CCD array is then read out and transmitted to the computer 18 for further processing. To improve the signal-to-noise ratio, an average may be taken from a plurality of CLSM A critical factor for the reliability of the evaluations just described is the tuning of the setting time of the rotating mirror to the scanning frequency of the CLSM. For this reason it is necessary to ensure that the rotating mirror can react quickly enough to the variations with time of the diffuse reflection intensity which correspond to the structure of the examined sample. If a local resolution of 5 pixels is required for the spectroscopic allocation and the CLSM image has a resolution of 512*512 pixels and an image frequency of 1 Hz, a mirror setting time of about 20 μsec is required. If the image frequency is reduced, e.g. to 0.05 Hz, a mirror setting time of about 0.4 msec is adequate.

Example 2 describes electronic sorting of the Raman scatter intensities.

Figure 3:
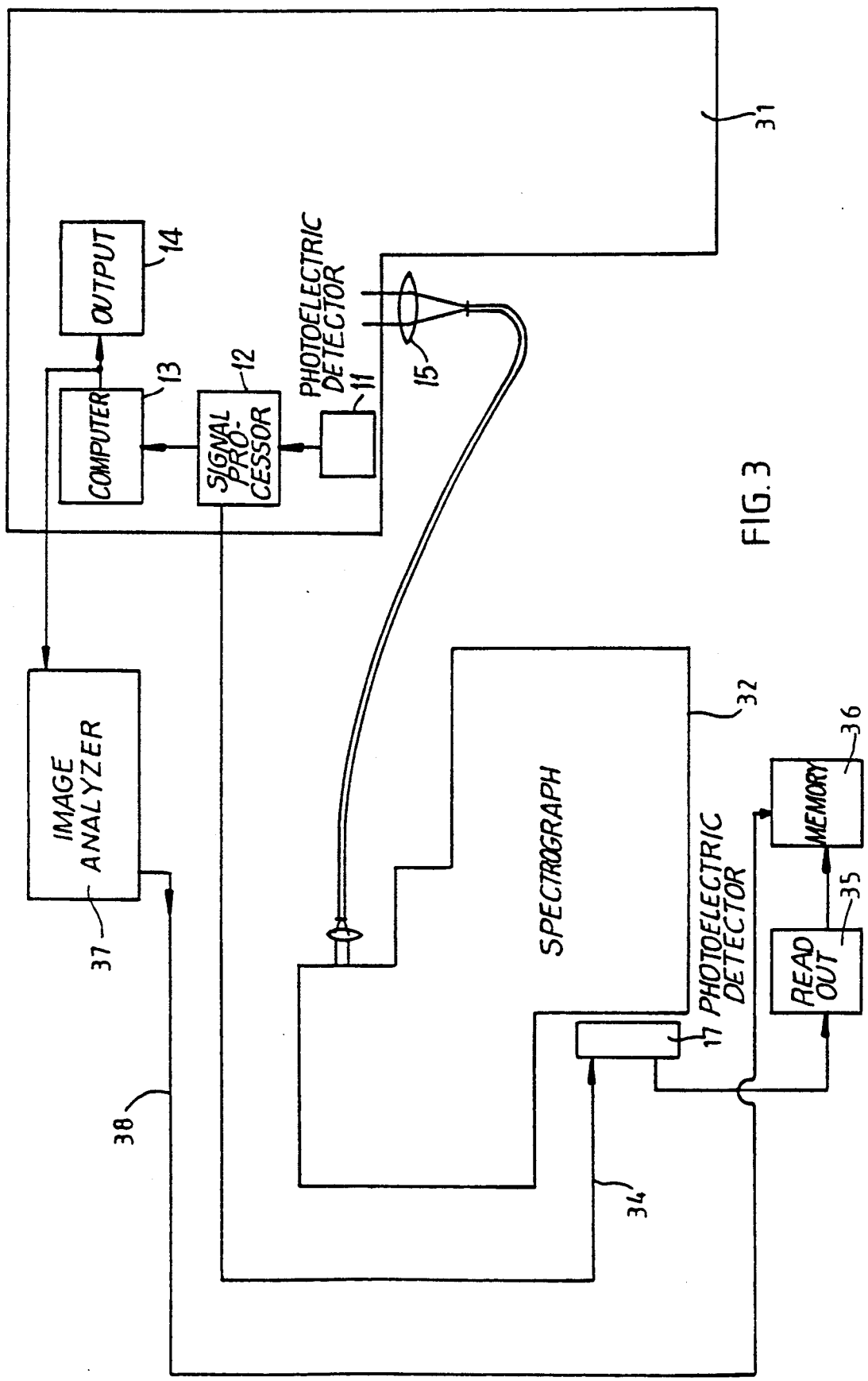
FIG. 3 illustrates how the process is effected with electronic allocation of the spectra to the pixels.

The technical implementation details of this example are illustrated in FIG. 3.

The optical and optoelectronic design of the confocal laser scanning microscope 31 and of the spectrograph 32 is identical to the arrangement described in Example 1. In this example, the Raman (and fluorescence) intensity emerging from the spectrograph directly strikes a one-dimensional CCD array 17 with 1,024 elements. Spectrum analysis of the spectrograph is so selected that the relevant spectral region is just picked up by said CCD array.

Transfer of the Raman intensity from the primary photoelectric detectors to the output line is effected synchronously to detection of the actual CLSM image in that the synchronizing signal 34 of the CLSM electronics is transmitted to the CCD array. Said Raman intensities are amplified in the readout electronics 35 and result, after analog-to-digital conversion, in a data record of 1024*8bit=1 kB per pixel. Said data records are, synchronously to the building of the conventional CLSM image, added up in a memory array 36 of N locations each for 1 Kb. The number N usually lies in the region of $1<=N<=10$. Allocation is effected by means of a look-up table (LUT) in which one of the addresses 1 to N is input for each pixel. If allocation is effected by determining the intensity, resolved into N regions, of the light elastically scattered in the sample and measured in the second stage of the spectrometer, said allocation may be easily achieved by a single scan of the sample by, for example, using the intensity signal, which in the first example controlled the mirror, to address the memory locations of the Raman spectra in the memory array 36. Otherwise, the LUT is calculated in a step preceding pick-up of the Raman intensities:

For this purpose, a conventional CLSM backscatter image is taken of the same sample piece and transmitted to the image-analyzing system 37. Said device carries out image cleaning and image processing operations on said image, using methods to be defined in a problem-specific manner, with the aim of object identification. For example, all singly or doubly connected objects may be detected, which in themselves present an approximately equal backscatter intensity and are sufficiently distinct in this intensity from their environment and which moreover have a specific minimum size.

Figure 4:
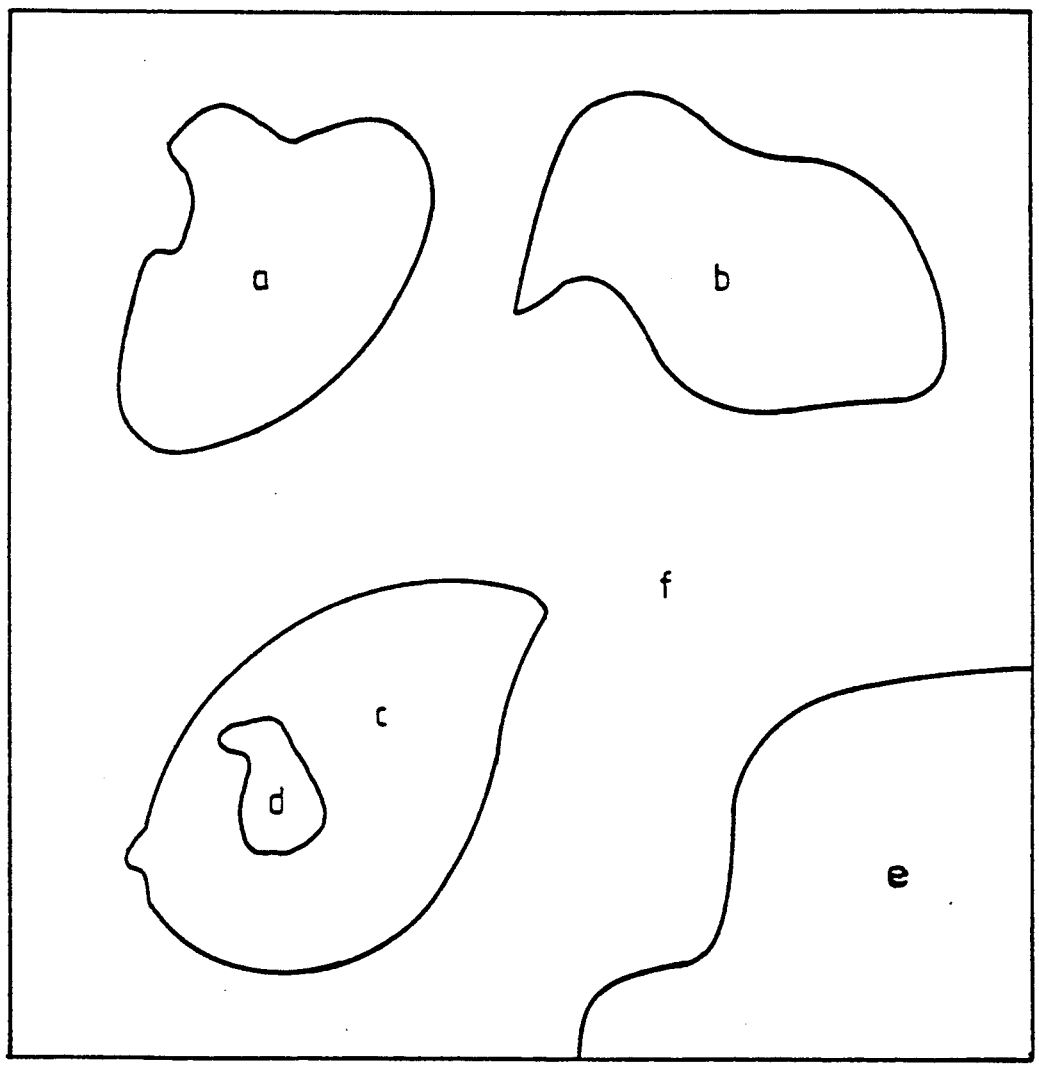
FIG. 4 shows the division of a sample image into five objects and the background by an image-analyzing system.

Thus, the imaged sample piece is divided into a number of objects and—residually—their environment. The latter may in turn comprise a plurality of sub-regions. In other words, the overall result is N objects, of which the image of the sample piece is composed. FIG. 4 reproduces a typical example of such a division (a, b, c, d, e and background f). If the number N is still too great for the subsequent Raman detection, the objects are classified on the basis of additional criteria. Finally, the objects or classes of object are allocated consecutive numbers. All that has to be done to set up the above-mentioned LUT is to determine for each pixel, to which of these N objects it belongs. Said LUT is then transmitted from the image-analyzing computer to the control electronics of the Raman signal detector 38.

On completion of the two steps:

a) production of the conventional CLSM image and image-analytical calculation of the LUT and b) pick-up of the Raman intensities separately for each of the objects defined under a), the Raman spectrum of each of the objects identified in the CLSM image may be analyzed. If the chemical composition of the sample as a whole is known, e.g. as a result of other analytical processes, the measured Raman spectrum of each of said objects may be compared with the known Raman spectra of the chemical constituents contained in the sample. In particular, using known mathematical methods (e.g. known from Appl. Spectrosc.33 (1979), p.351–357), the proportion of said chemical constituents in the individual objects of the CLSM backscatter image may be quantitatively determined.

I claim:

1. A process for producing image data for a sample, comprising the steps of:
   a. scanning a sample region with a confocal scanning light microscope to produce image data representing location and total light intensity of light reflected from each of a plurality of individual image elements;
   b. using a portion of the light reflected from each image element in a spectrometer to produce data for each image element representing reflected light intensity as a function of wavelength;
   c. dividing the total light intensity into a plurality of value ranges;
   d. correlating the data representing the light intensity as a function of wavelength for the plurality of image elements with the plurality of value ranges to produce a single mean spectrum for each value range for the entire spectra of all image elements which have a total light intensity in one such value range; and
   e. storing the location of each image element, the total light intensity thereof, a number corresponding to the value range the image element belongs to and the mean spectra of the plurality of value ranges in memory.

2. The process according to claim 1, wherein the data for each image element representing reflected light intensity as a function of wavelength is produced by measuring and digitizing with a photoelectric detector array and storing in a memory.

3. The process according to claim 1, wherein the data for each image element representing reflected light intensity as a function of wavelength is produced by focussing light as a line on a two dimensional photoelectric detector array and perpendicularly displacing the line on the array with a deflection unit within a beam path of the spectrometer in response to the intensity of the focussed light.

4. The process according to claim 2, wherein the photoelectric detectors comprise one or two dimensional photoelectric multipliers or light sensitive semiconductors.

5. The process according to claim 1, wherein the confocal scanning microscope has a monochromatic light source or a light source emitting a continuous spectrum.

6. The process according to claim 1, wherein the spectrometer is selected from the group consisting of Raman spectrometers and fluorescence spectrometers.

7. A process for producing image data for a sample, comprising the steps of:
 a. scanning a sample region with a confocal scanning light microscope to produce image data representing location and total light intensity of light reflected from each of a plurality of individual image elements of an image;
 b. using a portion of the light reflected from each image element in a spectrometer to produce data for each image element representing reflected light intensity as a function of wavelength;
 c. dividing the image into a plurality of objects;
 d. correlating the data representing the light intensity as a function of wavelength for the plurality of image elements with the plurality of objects to produce a single mean spectrum for each object for the entire spectra of all image elements which belong to one such object; and
 e. storing the location of each image element, the total light intensity thereof, a number corresponding to the object the image element belongs to and the mean spectra of the plurality of objects in memory.

8. The process according to claim 7, wherein the data for each image element representing reflected light intensity as a function of wavelength is produced by measuring and digitizing with a photoelectric detector array and storing in a memory.

9. The process according to claim 8, wherein the photoelectric detectors comprise one or two dimensional photoelectric multipliers or light sensitive semiconductors.

10. The process according to claim 7, wherein the confocal scanning microscope has a monochromatic light source or a light source emitting a continuous spectrum.

11. The process according to claim 7, wherein the spectrometer is selected from the group consisting of Raman spectrometers and fluorescence spectrometers.

* * * * *